United States Patent [19]

Utterberg

[11] Patent Number: 5,578,070
[45] Date of Patent: Nov. 26, 1996

[54] BLOW MOLDED VENOUS DRIP CHAMBER FOR HEMODIALYSIS

[75] Inventor: David S. Utterberg, Seattle, Wash.

[73] Assignee: Medisystems Technology Corporation, Las Vegas, Nev.

[21] Appl. No.: 594,775

[22] Filed: Jan. 31, 1996

Related U.S. Application Data

[63] Continuation of Ser. No. 272,101, Jul. 7, 1994, abandoned, which is a continuation-in-part of Ser. No. 876,041, Apr. 30, 1992, Pat. No. 5,328,461.

[51] Int. Cl.$^6$ .................................................. A61M 5/14
[52] U.S. Cl. ................................. 604/80; 604/4; 210/239
[58] Field of Search ............................ 604/4–7, 80–86, 604/251–255, 283; 55/193, 201; 128/DIG. 13; 210/239, 137, 767

[56] References Cited

U.S. PATENT DOCUMENTS

| | | |
|---|---|---|
| 1,664,938 | 4/1928 | McDonnell . |
| 2,704,544 | 3/1955 | Ryan . |
| 2,758,597 | 8/1956 | Elder . |
| 2,962,193 | 11/1960 | Totten . |
| 3,287,885 | 11/1966 | Sommer . |
| 3,342,019 | 9/1967 | Smythe . |
| 3,527,572 | 9/1970 | Urkiewicz . |
| 3,795,088 | 3/1974 | Esmond . |
| 4,048,995 | 9/1977 | Mittleman . |
| 4,293,413 | 10/1981 | Schnell . |
| 4,335,711 | 6/1982 | Olson . |
| 4,345,999 | 8/1982 | Sigdell et al. . |
| 4,622,032 | 11/1986 | Katsura et al. . |
| 4,643,713 | 2/1987 | Viitala . |
| 4,666,598 | 5/1987 | Heath et al. . |
| 4,681,606 | 7/1987 | Swan, Jr. et al. ............... 604/4 |
| 4,695,272 | 9/1987 | Berglund et al. . |
| 4,705,505 | 11/1987 | Fried . |
| 4,734,269 | 3/1988 | Clarke et al. . |
| 4,832,690 | 5/1989 | Kuu . |
| 5,019,723 | 5/1991 | Tran . |
| 5,061,236 | 10/1991 | Sutherland et al. . |
| 5,061,365 | 10/1991 | Utterberg . |
| 5,163,922 | 11/1992 | McElveen, Jr. et al. . |
| 5,176,633 | 1/1993 | Sit et al. . |
| 5,328,461 | 7/1994 | Utterberg .................... 604/80 |

FOREIGN PATENT DOCUMENTS

| | | |
|---|---|---|
| 0033080 | 1/1981 | European Pat. Off. . |
| 0958325A1 | 1/1982 | European Pat. Off. . |
| 0058325 | 1/1982 | European Pat. Off. . |
| 80610 | 6/1983 | European Pat. Off. . |
| 0318993 | 12/1988 | European Pat. Off. . |
| 0350675 | 6/1989 | European Pat. Off. . |
| 0587251A1 | 5/1990 | European Pat. Off. . |
| 0443963A1 | 2/1991 | European Pat. Off. . |
| 0496547A1 | 1/1992 | European Pat. Off. . |
| 2913301 | 11/1979 | Germany . |
| 1242938 | 5/1994 | Italy . |
| 1408319 | 12/1972 | United Kingdom . |
| 1544810 | 6/1976 | United Kingdom . |
| 2186799 | 11/1986 | United Kingdom . |
| 2176717 | 1/1987 | United Kingdom . |
| WO81/01793 | 7/1980 | WIPO . |
| WO86/02825 | 10/1985 | WIPO . |
| WO93/11808 | 11/1992 | WIPO . |

OTHER PUBLICATIONS

Printed sheet entitled Drake–Willock 7000 or 7200.

Primary Examiner—Randall L. Green
Assistant Examiner—Ceralin Smith
Attorney, Agent, or Firm—Gerstman, Ellis & McMillin, Ltd.

[57] ABSTRACT

A blow molded, rigid plastic venous chamber for hemodialysis, for use in a venous hemodialysis set. The chamber defines a plurality of first access ports adjacent to a first end thereof. A second access port is provided at an opposed end. A tubular plastic filter is positioned in close-fitting relation within the second access port to project into the chamber. Unique advantages are provided by such a blow-molded, filter-carrying chamber, and by the chamber shape.

36 Claims, 4 Drawing Sheets

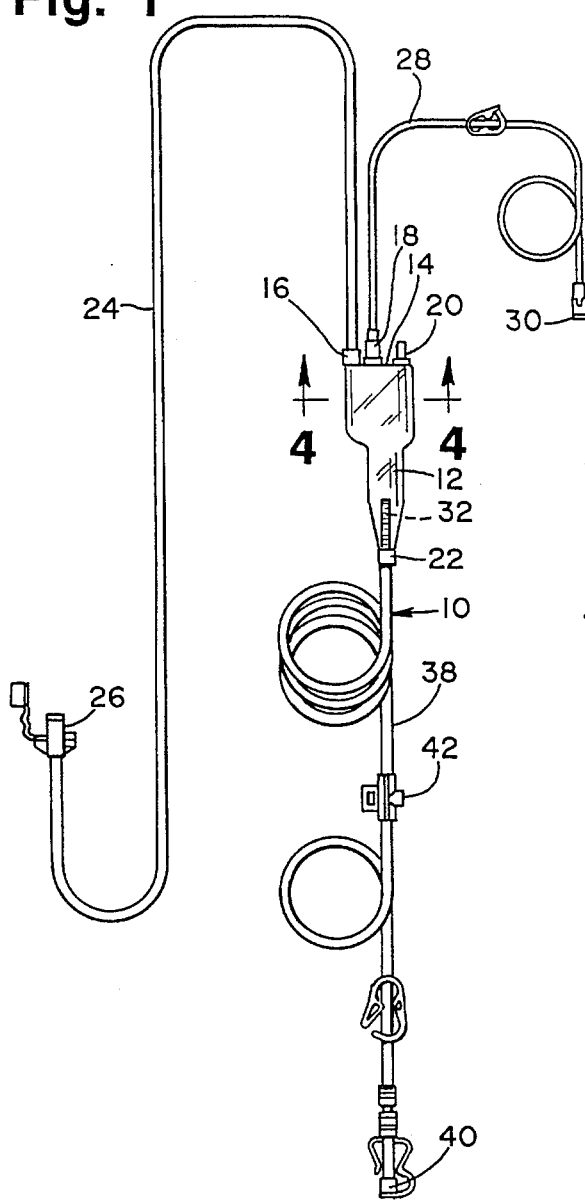
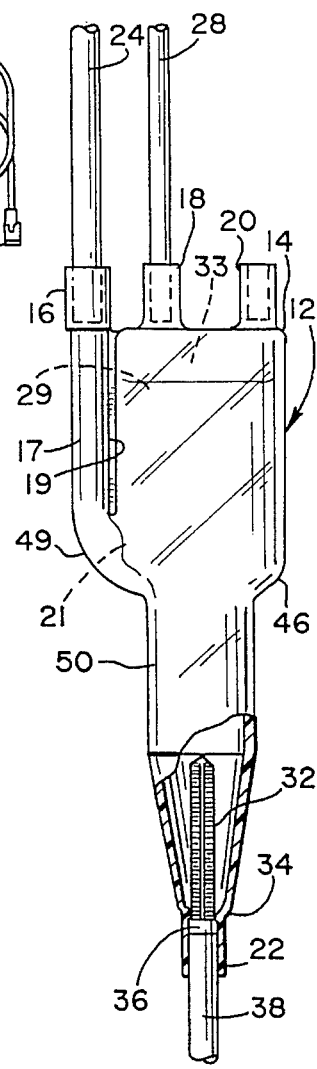
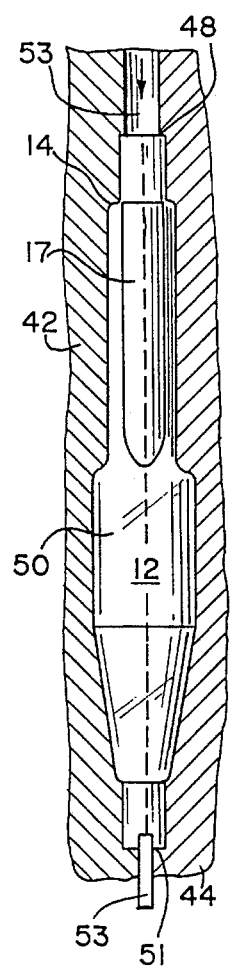
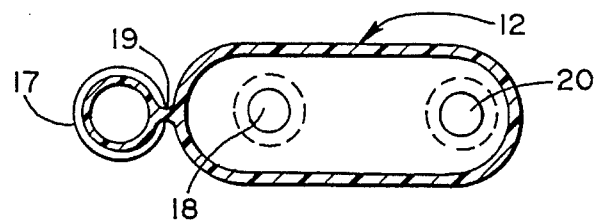

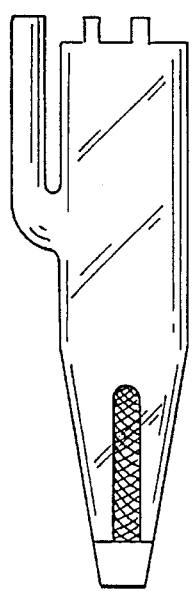
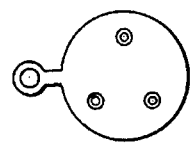
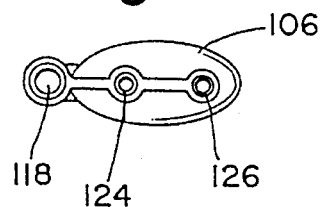
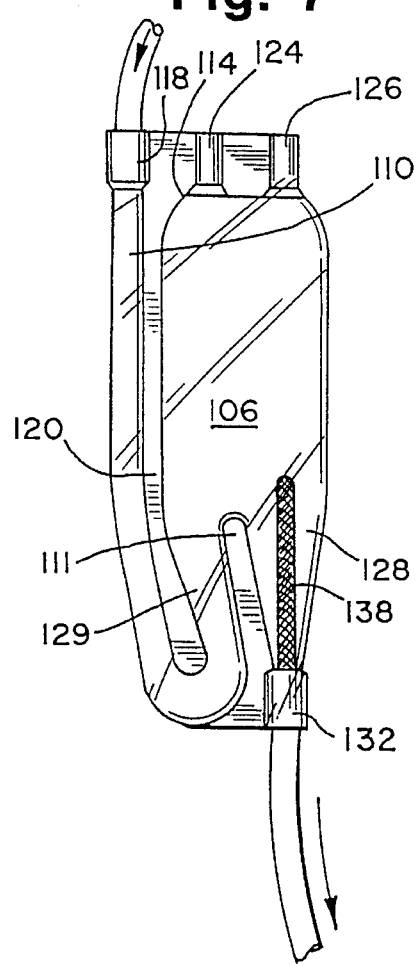
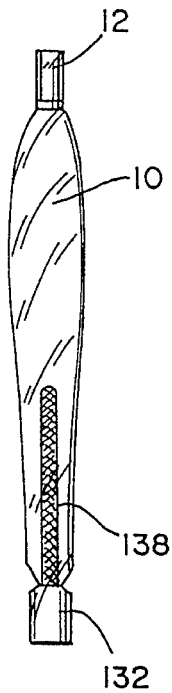

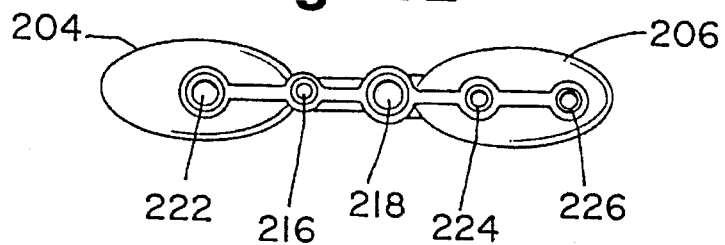
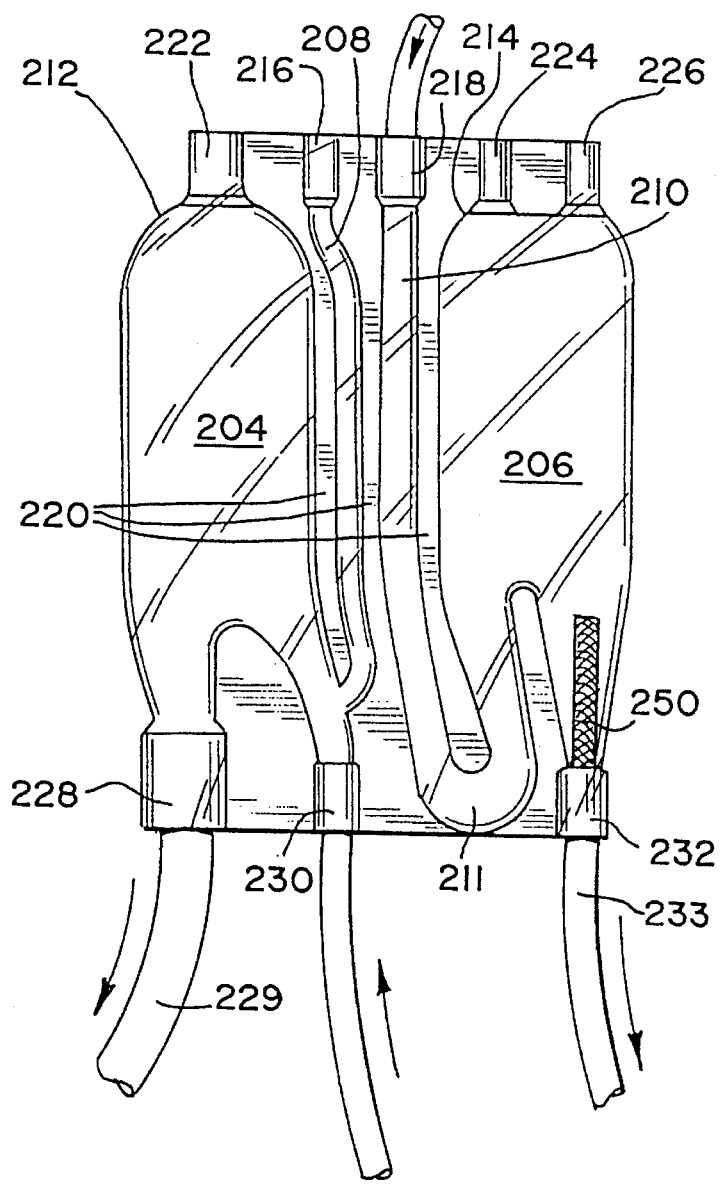

BLOW MOLDED VENOUS DRIP CHAMBER FOR HEMODIALYSIS

This is a continuation of U.S. application Ser. No. 08/272,101, filed Jul. 7 1994 now abandoned, which is a continuation-in-part of U.S. application Ser. No. 07/876,041, filed Apr. 30, 1992, now U.S. Pat. No. 5,328,461.

BACKGROUND OF THE INVENTION

In the well-known medical procedure of hemodialysis, blood is collected from a vascular access of a patient, passing through a well-known arterial hemodialysis set by means of a blood pump, to the hemodialyzer. The blood passes through hemodialyzer into a well-known venous hemodialysis set, by which the blood is conveyed back to the vascular access of the patient. Pediatric flow rates are as low as 20 ml/min while adult flow rates are as much as 650 ml/min. This entire set-up is known as an extracorporeal circuit.

The venous hemodialysis set has a well-known venous blood chamber, a so-called drip chamber that is typically 80–120 mm long and 17–25 mm outer diameter, designed to contain typically 7–35 ml of blood as a flow-through reservoir and operated such that blood does not completely fill the drip chamber. The chamber top has a blood inlet tube connection port in axial orientation communicating through the top to a blood inlet downspout in the main cavity of the chamber. The downspout length may vary such that the downspout outlet is either above the blood level (i.e. in the airspace), or beneath the blood level. Blood exits the venous chamber at the bottom by an outlet communicating axially through the bottom to a blood outlet tube connection port. A filter is placed within the chamber just above the blood outlet.

The venous drip chamber serves a number of functions:

1. Air bubbles contained in the incoming blood flow are forced by their buoyancy and reduction in velocity to rise to the air space. Flow out of the chamber is thereby degassed.
2. Blood pressure can be measured via a pressure monitor tube communicating through the chamber top into the air space.
3. Air or foam is also prevented from exiting the chamber by an ultrasonic air/foam detector attached to the outside of the drip chamber or the outside of the tubing just below the venous chamber. The detector stops the blood pump and causes a clamp to close below the venous drip chamber if air or foam is sensed.
4. Medicament tube access ports or injection sites are located on the chamber top, communicating with the air space.
5. Clots, etc. are prevented from leaving the chamber by the presence of a filter adjacent the exit of the chamber.

Currently, venous chambers are injection molded of flexible or rigid plastic, typically comprising a gently conical shape with an open end which is closed with a solvent-sealed top cap, after a plastic filter has been inserted through the open end and placed into snap-fit relation with the chamber near the bottom end. Snap-fit is required because, typically, the filter material is not compatible for solvent bonding with the chamber material. Thus it is retained by detents on the inside of the chamber. This is an imperfect solution since:

1. Such a filter can occasionally come loose (when blood pressure expands the flexible chamber) and/or
2. The space between the filter attachment ring and the chamber wall fills with blood which stagnates, promoting clots. The scientific literature (e.g. Ogden) reports such filters actually generate more clots than they trap.
3. Assembly is difficult and costly because the filter must be inserted with enough force to surmount the detents.

Disadvantages of injection molded chambers and top caps include:

1. Leaks between the top cap and the chamber body.
2. Clots promoted by blood foaming in its free-fall from a short downspout at flow-rates typically above 250 ml/min. The common name of "drip chamber" came about because at low flow rates the blood "dripped" from a short downspout opening to the blood level. More recently, flow rates of up to 650 ml/min have become possible because of newer hemodialyzers. But short downspouts foam severely at fast flow rates due to turbulence and cavitation caused by the rapid, continuous free fall of blood. Foam leads to increased clots due the greater surface area of an air/blood interface.
3. Clots promoted by blood stagnating in the space between long downspouts and the chamber wall. Long downspouts with an outlet beneath the blood level have been developed more recently in an attempt to reduce turbulence, in the same manner a hose dipped into a bucket of soapy water will not foam. However, blood stagnates in the tight space between the downspout and the chamber wall. Stagnation frequently leads to clots.
4. Clots promoted by blood stagnating above the outlet of a long downspout. At slower flow rates, long downspouts are counterproductive because blood stagnates in the blood layer above the downspout outlet, resulting typically in clotting.
5. Excessive air/foam alarms at high flow rates with long downspouts. Entrained air bubbles in the incoming blood flow is projected far enough down into the chamber such that they are sensed by the air/foam detector, creating many alarms and stopping the blood pump. It is well known that clotting increases whenever the blood flow is stopped.
6. Injection molding typically provides a structure having fairly sharp angles and edges, which is generally undesirable in blood handling apparatus.

DESCRIPTION OF THE INVENTION

Blow molding a venous chamber overcomes many of these problems. Arterial chambers have long been blow molded, such as Swan et al. U.S. Pat. No. 4,666,598. These have many advantages over injection molded chambers:

1. Blow molding creates a one-piece chamber, eliminating the prevalence of leaks from bonding two pieces together.
2. The blood inlet and outlet may be molded in a variety of shapes and angles, not limited to the axial orientation of injection molding. Also, the opening of the inlet (or outlet) into the chamber cavity may be in the chamber sidewall or chamber bottom rather than in a downspout separate from the chamber wall. Thus, no stagnant areas are created. Further, the inlet blood tube connecting port may be remote from the inlet opening to the chamber cavity. For example, the inlet blood tube connecting port may be in lateral relation to the chamber top while the inlet to the chamber cavity may be at the bottom, connected to the tube port via a conduit molded laterally to the chamber body.

It has long been known that a bottom inlet opening (causing upward flow into the chamber cavity) eliminates most causes of arterial chamber foaming, stagnation and clotting. The inlet flow is upward away from the bottom outlet (thus directing any entrained bubbles to the surface). No separate "upspout" within the chamber cavity is required, thus eliminating stagnation between the wall and chamber. And blood enters beneath the surface of the blood, eliminating any free-fall of blood, yet keeping all the blood in the chamber in gentle mixing eliminating stagnation.

3. Non-tubular shapes may be chosen to aid in preventing stagnant areas or turbulent areas. Many of these shapes are impossible by injection molding.

These advantages, however, have not been available before in a venous chamber:

1. Heretofore there has been no known way to place a filter into a blow molded chamber. Venous chambers require a filter.
2. Venous chambers must be of flexible material if they are to fit properly to air/foam detector probes. A flexible chamber is more difficult to blow mold as the parison sags more easily before it is blown.
3. A blood inlet opening at the bottom results in a non-tubular shape which cannot fit in current chamber holders for air/foam detectors.

By this invention, a blow-molded, flexible or semi-rigid plastic venous chamber for hemodialysis is provided. The chamber defines a plurality of first access ports substantially adjacent to a first chamber end, one of which is a blood tube inlet port. A blood tube exit port is provided at substantially the opposed end of the chamber. By this one aspect of the invention, a tubular plastic filter is positioned in close-fitting relation within the exit port to project into the chamber.

By this means, the desired blow molded venous chamber may be provided, while carrying a filter in a manner which has not been previously successfully accomplished.

The blow molded chamber may define an outwardly-facing annular step with the exit port. The tubular plastic filter defines an outer end portion that carries a radially outwardly projecting annular flange, proportioned to slidingly pass through the exit port, but to engage the annular step to limit inward travel of the filter to a predetermined, innermost position.

Additionally, flexible tubing may be sealed, typically solvent sealed, to the exit port and within the port at a position outwardly of the plastic filter. By this means, the plastic filter may be retained within the exit port by the presence of the tubing.

Typically, the blood inlet port may be positioned in separate, lateral relation to the chamber, with a communicating conduit extending from the blood inlet port at the first end of the chamber toward the opposed end in such separate, lateral relation. This blood inlet conduit enters the cavity of the chamber at a position below the first end, either in the sidewall or in the opposed, second end. By this means, a blow molded chamber may carry at least three access ports, while being readily manufacturable by blow molding technology, and without resulting in a blow molded chamber of unduly enlarged cross section.

Preferably, a portion of the blow molded venous chamber adjacent its first end is relatively flat and wide in cross section, when compared with a portion of the chamber below where the blood inlet conduit enters the cavity of the chamber. By this means a number of benefits accrue:

1. The flattened, upper portion facilitates the wide spacing of the first ports in the first end of the blow molded chamber,
2. The tubular, lower portion allows the chamber to be placed in currently available air/foam detector equipment, which require a round, cross sectional fitment area.
3. The flattened, upper portion, in conjunction with a sidewall blood inlet to the chamber cavity, promotes gentle mixing of the blood at high or low flow rates.

Additionally, the blow molding technology which is utilized herein can provide blood-contacting inner portions thereof which are essentially free of sharp angles and edges. This facilitates the desirable, gentle handling of the blood as it passes through the hemodialysis set to which the chamber of this invention is attached.

The blow-molded flexible plastic venous chamber may be manufactured for use as part of a venous flow set for hemodialysis by blow molding a chamber having a plurality of first access ports adjacent one end, one of which is a blood tube connection port, and a second blood tube connection port at its other end. The blow molded chamber is then cooled, and a tubular plastic filter is inserted into the blood tube exit port in close-fitting relation, so that the filter projects into the blow molded chamber. The filter may be secured in the chamber.

Additionally, there may be formed in the blow molded chamber during the molding process an outwardly facing, annular step within the second access port. The tubular plastic filter may define an outer end portion that carries a radially outwardly projecting annular flange which is proportioned to slidingly pass through the exit port, but which is large enough to engage the annular step. This limits the inward travel of the filter to a predetermined, innermost position. Then, blood tubing of a set may be sealed in the exit port behind the filter and annular step, to secure the filter in position.

The plastic venous chamber of this invention may then be assembled into a venous set for hemodialysis, to exhibit the numerous advantages discussed.

DESCRIPTION OF THE DRAWINGS

In the drawings, FIG. 1 is a plan view of a venous hemodialysis set which carries a blow-molded chamber of this invention;

FIG. 2 is an enlarged, side elevational view of the chamber of FIG. 1, shown in the process of being blow molded;

FIG. 3 is an elevational view, rotated 90 degrees from the view of FIG. 2, of the chamber after blow molding, with the filter inserted, and also showing connection with the various tubings of the venous set;

FIG. 4 is a transverse sectional view taken along line 4—4 of FIG. 1;

FIG. 5 is an enlarged, elevational view of a blow molded chamber generally tubular in shape;

FIG. 6 is an enlarged, top end view of the blow molded chamber of FIG. 5;

FIG. 7 is an enlarged, elevational view of a blow molded chamber with the blood inlet conduit entering the chamber cavity from the second opposed end, with the filter inserted;

FIG. 8 is an enlarged, side elevational view of the chamber of FIG. 7;

FIG. 9 is an enlarged, top end view of the chamber of FIG. 7;

FIG. 10 is an enlarged, elevational view of a blow molded cassette carrying an arterial and venous chamber;

FIG. 11 is a side elevational view of the cassette of FIG. 10;

FIG. 12 is a top, plan view of the cassette of FIG. 10; and

DESCRIPTION OF SPECIFIC EMBODIMENTS

Figure 13:
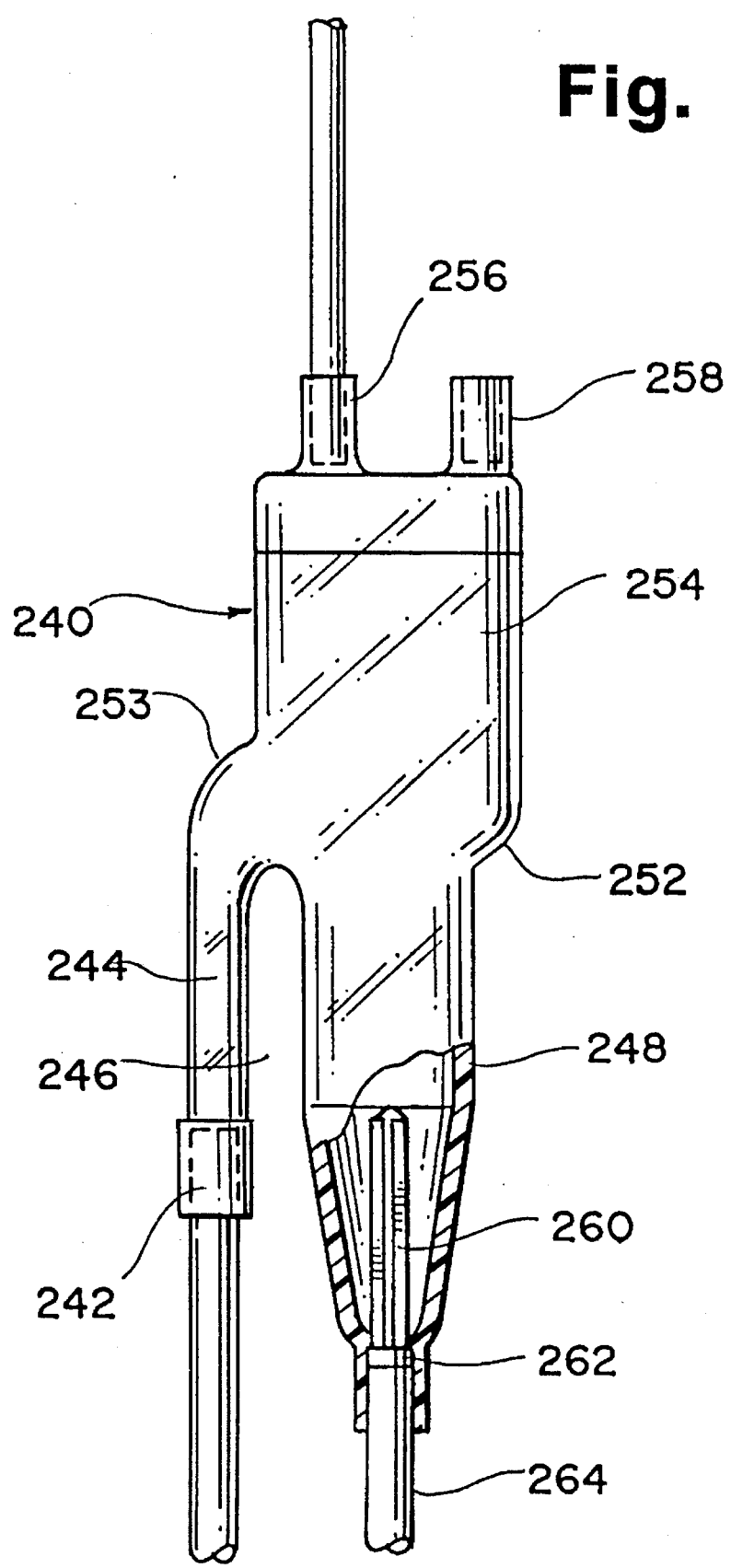
FIG. 13 is a side elevational view of another embodiment of a blow molded chamber of this invention.

Referring to the drawings, FIG. 1 shows a venous hemodialysis set 10 which may be generally conventional in design except for blow molded plastic chamber 12 of this invention and its relationship with set 10.

Blow molded plastic chamber 12, as shown, comprises a first end 14 defining three separate first access ports 16, 18, 20.

Plastic chamber 12 also defines a second access port 22 at the end opposed to the first end 14.

Blow molded venous chamber 12 may be blow molded from a parison of flexible or rigid, plastic such as rigid polyvinyl chloride, or poly(ethylene terephthalate), particularly a glycol-modified variety of the latter. Suitable plastic formulations for this purpose are commercially available.

Access port 16 of chamber 12 communicates with flexible tubing 24, with tubing 24 typically being sealed within port 16. Tubing 24 at its other end carries a conventional connector 26, which is adapted for connection with the blood outlet port of a hemodialyzer.

Access port 18 is connected to pressure monitor tubing 28, which carries at its opposed end a conventional connector 30 for a pressure monitor.

Access port 20 may comprise a conventional needle pierceable partition of resealable elastomer, of a conventional design.

Second access port 22 is shown to carry a tubular plastic filter 32, which is proportioned to be inserted through second access port 22, as shown in FIG. 3. The interior of second access port 22 defines an internal, annular step 34. Rear flange 36 of filter 32 engages the outer surface of step 34, so that it is restrained from further inward motion into chamber 12. Flexible tubing 38 also enters into port 22 within the port at a position outwardly from plastic filter 32 and flange 36. Thus, the inner end of tubing 38 causes plastic filter 32 to be retained within second access port 22 by the presence of such tubing. Tubing 38 may be conventionally solvent sealed in its position in second port 22.

The opposed end of tubing 38 defines a conventional connector 40 for connection to a fistula needle, which, in turn, penetrates the fistula of the patient for return of dialyzed blood.

Injection site 42 is also carried on tubing 38, and may be of conventional design.

Access port 16 is shown to be carried on a separate, generally longitudinal arm 17 of chamber 12, which is separated from the remainder of chamber 12 by partition line 19. Partition line 19 is formed during the blow molding process so that tubular section 17 is approximately cylindrical in shape. Then, tubular section 17 communicates with the remainder of the chamber 12 at a lateral flow position 21 which is between the first end 14 and opposed end 22. By this means, a third port may be provided to the first end of chamber 12 without undue crowding of the respective ports.

Turning particularly to FIG. 2, the shape of the molded chamber 12 from the side is shown. It can be seen that the area adjacent first end 14 is relatively flat and wide in cross section, by comparison of FIGS. 2 and 3, when compared with a portion 50 of the chamber which is spaced from first end 14, and typically which is adjacent opposed end 22. This facilitates the desired width and shape of portion 50 to fit into currently available machines with air/foam detectors requiring such a width and shape, while the area adjacent first end 14 does not provide undue volume or taking excessive amount of space to accommodate the three ports at first end 14.

Also, FIG. 2 shows the blow molding process of chamber 12 from a hot parison which is being repeatedly applied to the blow mold halves 42, 44 by a conventional extrusion means. As is conventional, the blow mold halves open, and the hot parison from the extruder is advanced into the space between blow mold halves 42, 44. The blow mold halves then close, pinching the parison at their respective ends 48, 51, or, additionally their sides 46, 49, while also forming partition 19 in the molding chamber. Then, compressed air or the like is conventionally inserted through blow tube 53 leading to first ports 16, 18, 20 and second port 22 respectively, to inflate the parison, so that the parison expands to the confines of the molding chamber defined with the blow mold halves 42, 44. This position is held until the parison has cooled sufficiently to form the desired chamber 12 of this invention.

Following trimming by conventional means, as shown in FIG. 3, plastic filter 32 may be inserted through second port 22, followed by insertion of tubing 38 which is sealed in place so that flange 36 is trapped between step 34 and tubing 38 for retention of the plastic filter in desired position.

The remaining tubings 24, 28 may be sealed into their respective ports, and the components of the injection site may be applied to port 20.

Thus, by this means, a venous hemodialysis set may be manufactured in which a blow molded chamber, having an inserted filter 32, is provided. The significant advantages of such a chamber are as discussed above. Specifically, the chamber of this invention may be made substantially free of sharp angles and edges at its blood-contacting inner portions. This is easily accomplished in blow molding as an inherent characteristic thereof, while such is not the case with respect to injection molded components. Also, the specific shape of the chamber of this invention permits chamber 12 to be of relatively small size and internal volume, while providing adequate cross section to accommodate three ports on first end 14. The entry of blood through port and conduit 16, 17 and along curved wall 49 into a flattened, central portion of the chamber by smooth, radiussed horizontal inlet 21 provides advantages, in that blood velocity is dissipated in its horizontal travel across the flattened cross-section and when it is turned upward by the gentle, radiussed curve of shoulder 46. Flow will form a gentle counterclockwise pattern in the flattened section adjacent the first end. Any entrained air bubbles will outgass at the blood surface 29 to join the airspace 33. Further, at low flow rates the blood above inlet 21 will not become stagnant owing to the counterclockwise pattern, nor at high flow rates will undue turbulence be allowed as the velocity is dissipated. Further, there is no stagnation area between the conduit 17 and chamber wall as there is between an injection molded downspout and chamber wall. This invention allows one chamber suitable for high or low flows, for all current machines.

FIGS. 5 and 6 show a chamber similar to FIGS. 1–4 except the cross sectional shape is substantially cylindrical in nature throughout its length.

Referring to FIGS. 7 through 9, there is shown a blow molded venous chamber suitable for a class of dialysis machine where the air/foam detector is mounted below the chamber and its ultrasound probes are mounted on the tubing below the chamber. Here, blow molding may be of a more rigid plastic because the ultrasound probes do not touch the chamber wall, and the blood inlet to the main cavity of the chamber may be at the end opposed to the first end 114. The entry of blood through access port 118 is shown to be carried on a separate, generally longitudinal arm 110 of chamber 106, which is separated from the remainder of chamber 106 by partition line 120. Partition line 120 is formed during the blow molding process so that tubular section 110 is approximately cylindrical in shape. Then, tubular section 110 communicates with the remainder of the chamber 106 at a position opposite of the first end 114.

Second access port 132 is shown to carry a tubular plastic filter 138 which is proportioned to be inserted through second access port 132, and retained in a manner similar to filter 32 of FIG. 3. A partition 111 is also formed between blood inlet 129 and blood outlet 128. The partition 111 may be curved or pointed away from outlet 128. Looking at FIG. 8 in conjunction with FIG. 9, one can see that inlet 129 and outlet 128 are of preferably outwardly tapering cross section. In the case of blood entering the chamber via conduit 110, the velocity is dissipated by a U-turn, as well as the outwardly tapering cross section in inlet 129.

Relatively rigid, plastic material may be used for these reservoirs. Such material typically maintains its shape as a hot parison much better than flexible material. Savings in time and cost are provided. Also, by the inventive chamber shape, the blood flow is gentle, unturbulent, but efficiently degassed before exiting the chamber.

In FIG. 10 is shown a blow molded cassette incorporating an inventive venous chamber. This blow molded cassette comprises a single parison having a pair of spaced chambers, with chamber 204 being typically the arterial prepump chamber, and chamber 206 being typically the venous chamber. Blood inlet 230 receives blood from an arterial connector such as connector 26, while blood outlet 228 connects directly to pump tubing 229. Likewise for venous chamber 206, blood comes in from the venous connector of the dialyzer to inlet port 218, which connects to a separate conduit 210 that extends the length of the chambers 204, 206, forms a U-turn at 211, and enters the venous chamber 206. Blood outlet 232 from the venous chamber passes through filter 250 which may be of a structure and mounting similar to filter 32 in FIGS. 2 and 3, with the blood traveling from there through tubing 233 to the venous patient connector. Depending upon whether the system is used in a prepump or a postpump manner, saline or heparin can be inserted into inlets 216, 224, or 226. Conduit 208 which is separate from the chambers extends into the port area 230 of chamber 204. Flattened areas 220 are also defined by the blow mold to provide the discrete chambers 204, 206, and conduits 208, 210.

Thus, by the embodiment of FIGS. 10–12 it can be seen that the prepump chamber and the postpump chamber, as well as their various ports, can be formed into a single blow molded cassette from a single parison.

Referring to FIG. 13, another embodiment of a blow molded blood chamber is shown, being generally similar in construction to the chamber of FIG. 3 except as otherwise indicated herein.

Blood chamber 240 may be blow molded as in the previous embodiment, having an access port 242 which receives blood as the inlet. Access port 242 represents the end of a downwardly extending side conduit 244 which is integral with the rest of chamber 240 at one end, but which may be laterally separated from the chamber by either a flattened plastic section or preferably a space 46. Space 246 is wide enough to permit lower portion 48 of the chamber to fit into the currently available air/foam detectors as in the previous embodiments. Alternatively, conduit 244 can be bent out of the way when chamber 240 is placed in an air/foam detector.

Inlet conduit 244 forms a horizontal bend so that inflowing blood is curved by curved surface 253 into horizontal flow. As before, the horizontally flowing blood then impinges curved surface 252 on the other side of blood chamber 240 to be gently urged upwardly into the upper chamber portion 254 with a swirling flow, as previously described with respect to previous embodiments. Added access ports 256, 258 are provided at one end of chamber 240 for purposes of connection with pressure monitor tubing and for needle access, as in previous embodiments.

At the bottom of lower chamber portion 248, a tubular filter 260 is provided, being secured into position in a manner similar to that described with respect to the FIG. 3 embodiment. Thus, blood flows downwardly through filter 260 and then out of the outlet port 262 into flow tubing 264, for a continuation of the blood flow path.

The above has been offered for illustrative purposes only, and is not intended to limit the scope of the invention of this application, which is as defined in the claims below.

That which is claimed is:

1. A blow-molded, flexible plastic blood chamber for hemodialysis, said chamber defining an inlet blood port adjacent an end of the chamber, an outlet blood port adjacent an opposed end of the chamber, and a tubular plastic filter positioned in close-fitting relation adjacent said outlet port to project into said chamber, in which an inward projection is defined within said outlet port, said tubular plastic filter defining an outer end portion that carries a radially outwardly projecting, annular flange proportioned to slidingly pass through said outlet port and engaging said inward projection to limit inward travel of said filter to a predetermined, innermost position, plus means for retaining said filter in said position.

2. The chamber of claim 1 in which said retaining means comprises flexible tubing sealed within said outlet port at a position outwardly of said plastic filter, whereby said flange and plastic filter are retained within said outlet port by the presence of said tubing.

3. The chamber of claim 1 in which a portion of said chamber adjacent the end opposed to said filter is relatively oval in cross-section, when compared with the portion of said chamber adjacent to said filter.

4. The chamber of claim 1 in which said inlet port is positioned in separate, lateral relationship to said chamber and from which there extends a conduit toward one end of said chamber also in separate, lateral relation, said conduit communicating with said chamber at the conduit end opposed to the inlet port.

5. A venous hemodialysis set which includes at least one plastic, venous chamber of claim 1.

6. The chamber of claim 1 in which said inlet port is formed by a conduit which is laterally spaced from the remainder of said chamber except at an end of said conduit opposed to said inlet port.

7. The chamber of claim 6 in which said conduit opposed end communicates with the balance of said chamber in curved, angular manner.

8. A plastic, venous chamber for hemodialysis, having first and opposed ends said chamber defining a first access port adjacent an end of the chamber, a second access port adjacent an end of the chamber, and a tubular, plastic filter positioned in close-fitting relation with said second access port to project into said chamber, said first access port being positioned in separate, lateral relation to said chamber, and a lateral conduit extending from said first access port also in said separate, lateral relation, said conduit communicating with said chamber at a position between the first and opposed ends, and in which a portion of the chamber adjacent the chamber end opposed to the filter is relatively flat and wide in cross-section when compared with the portion of said chamber adjacent the end where said filter is located, and further in which an annular step is defined within said second access port, said filter defining an outer end portion that carries a radially, outwardly projection, an annular flange proportioned to slidingly pass through said second access port, but to engage said annular step to limit inward travel of said filter to a predetermined, innermost position.

9. The chamber of claim 8 in which flexible tubing is sealed to said second access port and within said port at a position outwardly from said annular flange of the plastic filter, whereby said plastic filter is retained within said second access port by the presence of said tubing.

10. The chamber of claim 8 in which the blood contacting inner portions of said chamber are essentially free of sharp angles and edges.

11. A venous hemodialysis set which includes at least one plastic, venous chamber of claim 8.

12. The plastic, venous chamber of claim 10 in which said first and second access ports are adjacent the same end of the chamber, said lateral conduit being physically separated from the remainder of said chamber except at an entrance port of said conduit with the chamber.

13. The chamber of claim 8 in which said first and second access ports are positioned at opposite ends of the chamber.

14. A flow molded, flexible plastic blood chamber for hemodialysis, said chamber defining an inlet blood port adjacent an upper end of the chamber and an outlet blood port adjacent an end of the chamber, said inlet port being positioned in separate, lateral relation with said chamber and having a conduit extending longitudinally of said chamber from said inlet port toward the end of said chamber opposed to the inlet port end in said separate lateral relation to said chamber, said conduit curving into communication with said chamber in a transverse direction at a position between the ends of said chamber, a portion of said chamber opposed to the area of communication of said conduit and chamber defining a sloping surface to turn lateral blood flow across said chamber gently upwardly, to define a gentle, circulatory flow of blood in said chamber.

15. The chamber of claim 14 in which a portion of said chamber opposed to the end which carries said outlet port is relatively oval in cross-section, and a portion of said chamber adjacent to the end which carries said outlet port is relatively circular in cross-section, said chamber defining a junction area adjacent said curved shoulder between said relatively oval and relatively circular sections.

16. The chamber of claim 14 in which an inward projection is defined within said outlet port, and a tubular plastic filter is positioned in said outlet port, said filter defining an outer end portion that carries a radially outwardly projecting, annular flange proportioned to slidingly pass through said outlet port, but to engage said inward projection to limit inward travel of said filter to a predetermined, innermost position, and flexible tubing sealed within said outlet port at a position outwardly of said plastic filter flange, whereby said flange and plastic filter are retained within said outlet port by said tubing.

17. A flexible plastic blood chamber for hemodialysis, said chamber defining a first blood inlet port adjacent an upper chamber end, and an outlet blood port at an opposed lower chamber end, said inlet port being positioned in separate, lateral relation with said chamber, a conduit extending vertically from said inlet port toward said opposed end in said separate, lateral relation, which conduit curves to communicate with the interior of said chamber in horizontal direction at an inlet position between said upper and lower ends, a portion of said chamber horizonally opposite to the inlet position of said conduit and chamber defining a sloping surface to turn horizontal blood flow from said conduit across said chamber gently upwardly, back toward said upper end of the chamber, to define a gentle, circulatory flow of blood in said chamber, said chamber defining below said inlet position a portion of substantially circular cross-section.

18. The chamber of claim 17 in which an inward projection is defined within said outlet port, and a tubular plastic filter is positioned in said outlet port, said filter defining an outer end portion that carries a radially outwardly projecting, annular flange proportioned to slidingly pass through said outlet port, but to engage said inward projection to limit inward travel of said filter to a predetermined, innermost position, and flexible tubing sealed within said outlet port at a position outwardly of said plastic filter flange, whereby said flange and plastic filter are retained within said outlet port by said tubing, said chamber being blow-molded.

19. The chamber of claim 17 in which a portion of said chamber above the inlet position is relatively oval in cross-section, when compared with the portion of said chamber adjacent to said outlet blood port.

20. The chamber of claim 17, comprising a part of a venous set for hemodialysis.

21. The chamber of claim 17 in which the sloping surface is positioned below most of the horizontal blood flow.

22. The chamber of claim 17 in which blood fills said chamber up to a level positioned above said inlet position and below said upper chamber end, there being a volume of gas positioned in said chamber above the blood level at said upper end.

23. The chamber of claim 17 in which said portion of circular cross section is longitudinally spaced from said conduit extending vertically from said inlet port.

24. The chamber of claim 17 in which said chamber defines an access port connected to pressure monitor tubing carried at the upper chamber end.

25. The chamber of claim 17 in which an inward projection is defined within said outlet port, and a tubular plastic filter is positioned in said outlet port, said filter defining an outer end portion that carries a radially outwardly projecting, annular flange proportioned to slidingly pass through said outlet port, but to engage said inward projection to limit inward travel of said filter to a predetermined, innermost position, and flexible tubing sealed within said outlet port at a position outwardly of said plastic filter flange, whereby said flange and plastic filter are retained within said outlet port by said tubing, said chamber being blow molded, said chamber also being filled with blood up to a level which is above said inlet position and below the upper end of the chamber.

26. The chamber of claim 25 comprising a part of a venous set for hemodialysis.

27. The chamber of claim 26 in which a portion of said chamber above the inlet position is relatively oval in cross section, when compared with at least a portion of said chamber below said inlet position.

28. The chamber of claim 26 in which said portion of substantially circular cross section is longitudinally spaced from said conduit extending vertically from said inlet port.

29. The chamber of claim 28 in which substantially the entire portion of said chamber below said inlet position is of circular cross section.

30. The method of removing gas bubbles from blood, which comprises: passing blood through an inlet port downwardly toward a chamber; passing said blood into said chamber in a horizontal flow at a point spaced from the chamber ends; causing horizontally flowing blood in said chamber to be directed upwardly by a an opposed, sloping surface within said chamber, to create a circulating flow of blood within said chamber; and causing blood to flow out of said chamber through an outlet port at the bottom of said chamber.

31. The method of claim 30 further Comprising passing blood through a filter while being drawn out of said chamber through said outlet port.

32. The method of claim 30 further comprising passing blood to the chamber while flowing vertically to a sloping surface which directs said blood horizontally into the chamber.

33. The method of claim 30 in which the main flow of horizontally flowing blood is directed upwardly by said opposed, sloping surface.

34. The method of removing gas bubbles from blood, which comprises: passing said blood through a curved path into said chamber in horizontal flow at an inlet position spaced from the chamber ends, said chamber being partially filed with blood and having a blood level above said inlet position; causing horizontally flowing blood from said inlet position in said chamber to be directed upwardly by a sloping surface within said chamber positioned below the main flow of said horizontally flowing blood, to create a circulating flow of blood within said chamber; and causing blood to flow out of said chamber through an outlet port positioned below said inlet position.

35. The method of claim 34 which further comprises positioning a lower portion of said chamber within an air/foam detector, said lower portion of said chamber being of circular cross section.

36. The method of claim 35 in which said blood is passed through a filter as it flows out of said chamber through said outlet port.

* * * * *